United States Patent [19]
Hanna

[11] 3,991,746
[45] Nov. 16, 1976

[54] PATIENT MONITORING SYSTEM AND METHOD

[75] Inventor: Harry Allen Hanna, Des Moines, Iowa

[73] Assignee: Medical R & D, Limited, Des Moines, Iowa

[22] Filed: Mar. 31, 1975

[21] Appl. No.: 563,487

[52] U.S. Cl. ............................ 128/2 S; 128/2.06 F; 128/2.1 Z; 128/DIG. 29; 340/258 C; 340/279
[51] Int. Cl.² ............................................. A61B 5/10
[58] Field of Search ................ 128/2 R, 2 S, 2.06 F, 128/2.08, 2.1 R, 2.1 Z, DIG. 29; 340/279, 258 B, 258 C, 258 R

[56] References Cited
UNITED STATES PATENTS

| | | | |
|---|---|---|---|
| 3,439,358 | 4/1969 | Salmons | 128/2 S |
| 3,545,429 | 12/1970 | Pelta et al. | 128/2.1 Z |
| 3,587,562 | 6/1971 | Williams | 128/2.1 Z |
| 3,613,670 | 10/1971 | Edenhofer | 128/2.06 F |
| 3,750,126 | 7/1973 | Solomon | 340/258 C |
| 3,898,981 | 8/1975 | Basham | 128/2 S |

*Primary Examiner*—William E. Kamm
*Attorney, Agent, or Firm*—Rudolph L. Lowell

[57] ABSTRACT

A patient monitoring system made of an enclosing cover of electrically insulating and waterproof material encloses two conductive foils separated by an insulating sheet. The upper foil, the one adjacent the patient, is connected to a circuit that applies a carrier frequency signal to the upper foil and uses the lower foil as an electrical shield. An amplifying circuit receives the carrier signal as it is modulated by the movements of a patient adjacent the upper foil and produces an amplified output. The amplified output is demodulated and interpreted by an output circuit that produces signals that monitor selected movements or body conditions of the patient.

21 Claims, 4 Drawing Figures

PATIENT MONITORING SYSTEM AND METHOD

BACKGROUND OF THE INVENTION

This invention relates to patient monitoring systems, particularly to such systems that use automatic sensing devices to provide a signal indicating the movements or absence of a patient, or body conditions of the patient.

It is to interest to hospitals and other institutions that the movements of persons confined to a bed or to any constrained location or position be controlled and monitored to indicate the physical activities and body condition of these persons. At present, elaborate arrangements are necessary to monitor many conditions of patients and often a desired or necessary monitoring is not used because of cost or unavailability of necessary equipment. Some prior art devices have been developed that use magnets attached to persons being monitored, physical connections of various types, or mechanically actuated switching devices that respond to the presence or absence of a patient from his bed or chair.

All of the known prior art devices suffer from various deficiencies. The need to make physical connections is obviously burdensome and is usually defeated by the activity of the patient. Also, these systems require special equipment so as to limit their availability to many hospitals. One device uses a capacitor that is deformed by pressure so that its capacitance changes when the deforming force is removed. This change is sensed to indicate the absence of the patient. However, this device is of limited application and requires a source of constant electrical potential.

SUMMARY OF THE INVENTION

With this invention a new monitoring system and method are provided that are capable of monitoring not only the presence or absence of a patient from a bed or the like, but is also capable of monitoring other body conditions such as respiration rate, pulse rate, violent movement that may indicate convulsions, and other movements that may be desired. The system can be used in conjunction with existing nurse call systems and by simply being plugged into the call system can provide any number of desired signals to indicate the occurrence of selected patient movements and conditions.

DETAILED DESCRIPTION OF THE INVENTION

The invention essentially comprises an electrical monitoring circuit and capacitive element device that has a conductive plate, or foil sheet placed adjacent to the patient. This conductive plate would typically be a conductive foil sheet placed inside of a cover, that has top and bottom electrically insulative and waterproof sheets sealed together at the perimeters thereof. Preferably a second electrically conductive foil sheet would be placed adjacent to the first foil sheet but separated therefrom by an electrically insulating sheet. This second foil sheet provides an electrical shield for the first foil sheet and would be located beneath the first foil sheet when the assembly is placed on the mattress of a bed so as to limit the electrical field around the first foil sheet to the area of the patient and to eliminate interfering signals.

A monitoring circuit is connected to the first conductive foil sheet to apply a carrier frequency signal thereto. Since any movement of the patient alters the electrical field created by the carrier signal this alteration appears as an impedance variation in the circuit. This impedance variation is applied to correspondingly modulate the carrier signal which is subsequently demodulated, amplified and interpreted to produce an alarm signal or to provide a monitoring signal for recording purposes.

Figure 3:
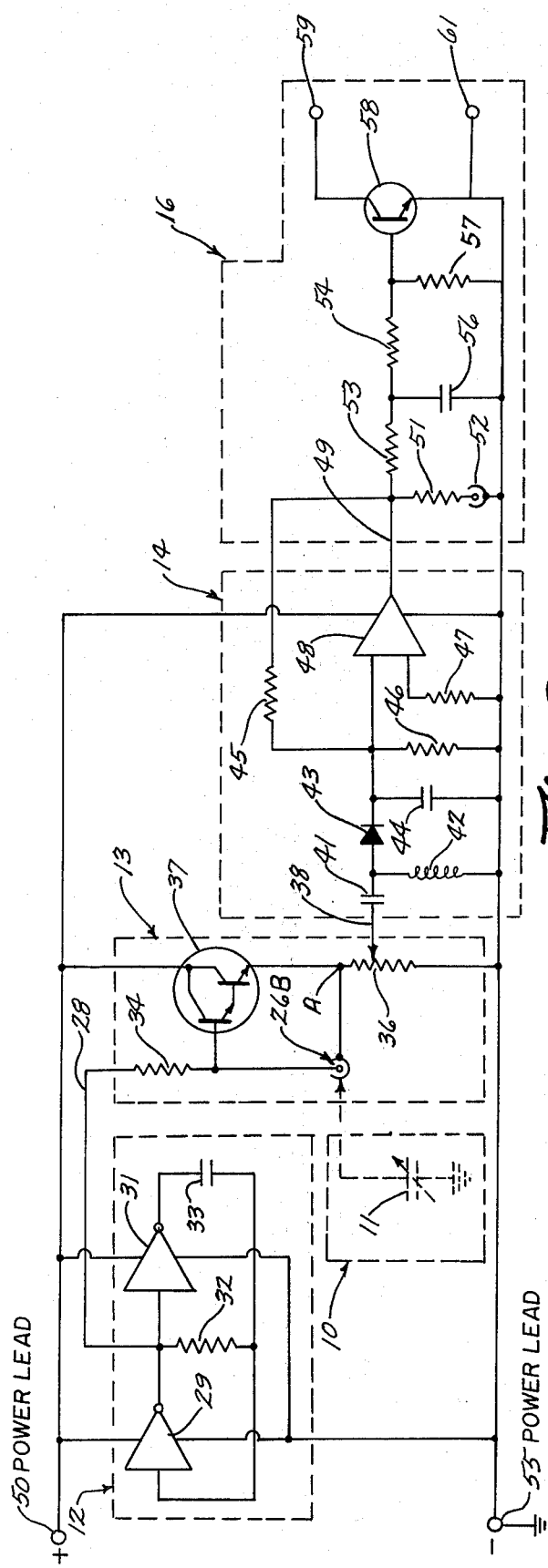
FIG. 3 is a schematic drawing of an embodiment of this invention.

Referring to FIG. 3, a patient monitoring system according to this invention comprises a capacitive element device 10, shown symbolically as comprising or producing a variable capacitance 11, a carrier means 12, an amplifying means 13, a demodulating means 14, and an output means 16.

Figure 1:
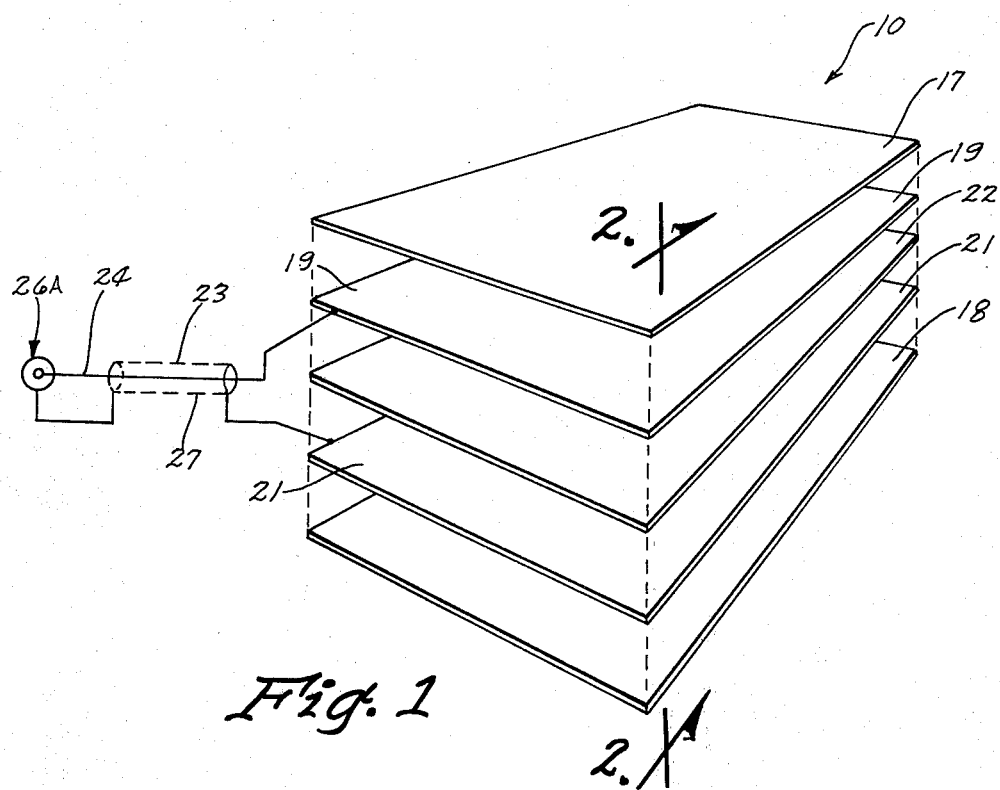
FIG. 1 is a diagrammatic showing of a capacitive element device that forms part of the system of this invention.
Figure 2:
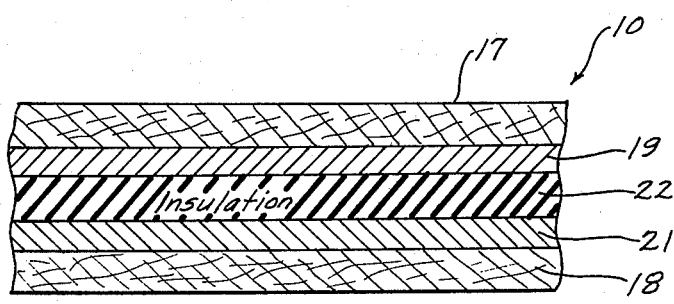
FIG. 2 is an enlarged detail sectional view on line 2—2 in FIG. 1 to more clearly show the capacitive of the conductive element.

Referring to FIGS. 1 and 2, the capacitive element device 10 comprises a pad device having an upper cover 17, a lower cover 18, an upper conductive sheet or foil 19, a lower shield sheet or foil 21 of conductive material, and an electrically insulating sheet 22. The construction of the cover may be of any type known in the art and would typically have the upper and lower covers 17 and 18 made of an electrically nonconductive material that is waterproof. The upper and lower covers are preferably connected and sealed together at their perimeters in any known manner so as to prevent separation of the cover or entry of foreign matter. The conductive sheets 19 and 21 may be foils, woven conductive material, overlapping plates or of any other known construction. The lower shield sheet 21 should be coextensive with or larger than the conductive sheet 19 so as to insure isolation of the conductive sheet 19 from undesirable spray signals toward the side thereof remote from the shield sheet 21. A shielded cable 23, or other suitable connecting device connects the device 10 to the remainder of the system. Cable 23 has an inner or center conductor 24 connected to the electrically conductive sheet foil 19 and connected to the electrically conductive sheet foil 19 and to a plug 26A connectable with a jack 26B in the amplifying means 13. The outer shielding conductor 27 of the cable 23 is connected to the lower shield sheet 21 and to the plug 26A.

As shown in FIG. 3, the capacitive element device 10 is connected to the jack 26B which forms part of the input circuit of the amplifying means 13. This input circuit also receives a signal from the carrier means 12 along a conductor, or connection 28. The carrier means 12 includes inverters 29 and 31, a resistor 32, and a capacitor 33. These components are connected to provide a carrier frequency output of a selected frequency determined by the values of resistor 32 and capacitor 33. The circuit shown produces a square wave output but other oscillating circuits could be used if desired. The output frequency is selected relative to the circuit used and to the patient condition to be monitored. Frequencies in the range of 10 to 30 kilohertz are generally suitable.

The carrier frequency signal from the conductor 28 is applied as an input signal to the amplifying means 13 which includes the jack 26B, a resistor 34, a potentiometer 36, and a high gain amplifying device such as a Darlington transistor 37. Resistor 34, jack 26B and pad device 10 make up a voltage divider circuit that produces the input for the transistor 37. The transistor 37 amplifies this input signal to produce an output at the conductor 38 which is an amplified carrier frequency signal modulated by the varying impedance produced at the jack connection 26B by the change in field or the change in the capacitive coupling produced by the movements or absence of the patient being monitored. The modulation takes place due to the fact that the impedance appearing in the voltage divider at the jack 26B varies as a function of the movements made by the patient. The sensitivity of the amplifying means 13 to the input signal is selected by the adjustment of potentiometer 36.

The modulated carrier frequency signal is received from a conductor 38 by the demodulating means 14 which comprises a capacitor 41, a coil 42, a detecting diode 43, a capacitor 44, a feedback resistor 45, an input bias resistor 46, an input bias resistor 47, and an amplifier 48. The demodulating means 14 detects the incoming signal by the rectifying effect of diode 43 and bypasses any residual carrier frequency through capacitor 44 to ground. Since the system is usable in any typical hospital environment a filtering circuit to eliminate any sixty hertz line current, such as may occur from a nurse call network or equipment supply lines, is provided by the capacitor 41 and coil 42. The demodulated and filtered signal is received at a level determined by the values of the input resistors 46 and 47 and by the amplifier 48 which produces an amplified demodulated signal at conductor 49. Power from the nurse call network or other suitable power source is connected to the system at the power leads 50 and 55.

The signal from the demodulating means 14 is received by the output means 16 which is of a type or form to interpret the demodulated signal. The output means may be selected, designed or combined in various ways to monitor many body characteristics manifested by movements, either voluntary or involuntary, of the patient. The output means 16 is thus exemplary of one of various output circuits that may be used to monitor patient movement. By adjusting the sensitivity of the amplifying means 13 through the adjustment of potentiometer 36 the type of patient body movement to be monitored may be selected. For example, with a comatose patient the sensitivity may be adjusted to respond to a low level of movement while with persons likely to have convulsive spasms the sensitivity would be adjusted to respond to a relatively high level of the more rapid body movements involved. Output means 16 is typical for monitoring such body movements at a selected level and includes a resistor 51, an output jack connection 52, resistors 53 and 54, a capacitor 56, a resistor 57 and a switching transistor 58 which produces a switching output signal across terminals 59 and 61.

The demodulated signal from the demodulating means 14 appearing at the conductor 49 is used to produce two outputs from the output means. A first output taken across the resistor 51 at the jack 52 is proportional to the output signal appearing at conductor 49. This output at the jack 52 can be used to provide a continuous recording of the movement being monitored on a visual instrument such as an oscilloscope or to provide a reviewable record on a chart recorder. This first output could also be used to provide an input to output circuits designed to respond to different patient body characteristics if a proper sensitivity level can be selected by adjustment of the potentiometer.

The second output of the demodulated signal is used to provide an alarm signal when the monitored patient body movements reach a selected level within a minimum selected time. To accomplish this interpretation of patient body movement the demodulated and amplified output signal is applied to a time delay circuit comprised of the capacitor 56 and resistor 53. Since the movements monitored will produce a signal at a level above a preselected level, as determined essentially by the sensitivity of the amplifying means and the input bias level to the amplifier 48, the output appearing at the conductor 49 will have a level which varies as a direct function of the degree of body movement being monitored. This signal charges capacitor 56 through the resistor 53 so that when the charge on the capacitor 56 reaches a selected level, determined by the resistances of the resistors 54 and 57, the transistor 58 will turn on to produce a switching signal at the terminals 59 and 61. Transistor 58 is shown schematically and may be connected in any configuration to produce the desired output or it may be a switching device that will perform the same general function. Unless the charging level on the capacitor 56 is maintained for some selected minimum time and level relationship, the capacitor 56 will not reach a level high enough to turn on the transistor 58 since the capacitor 56 can discharge through resistors 54 and 57 at a level below that necessary to turn on the transistor 58. The turning on of the transistor 58 can be used to activate a visual or audible alarm but other responses could be made such as the turning on of a recorder that would begin monitoring from jack connection 52.

Figure 4:
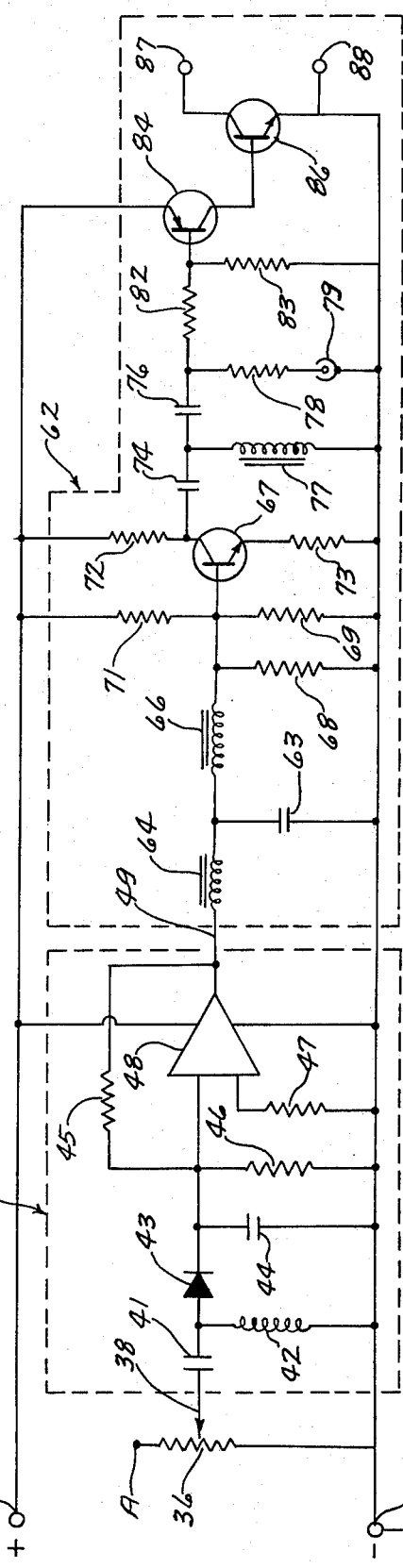
FIG. 4 is a schematic drawing of another embodiment of this invention.

Referring to the embodiment of the invention shown in FIG. 4, the output means 62 is adapted to monitor a cyclic body condition such as a pulse rate or respiration rate. Output means 62 includes a first filtering circuit comprised of a capacitor 63, choke coils 64 and 66, and an amplifying circuit that has a transistor 67 and resistors 68, 69, 71, 72 and 73; and a second filtering circuit comprised of capacitors 74 and 76 and a choke coil 77, a monitoring output circuit having a resistor 78 and an output jack connection 79, and a switching circuit that includes resistors 82 and 83, a driver transistor 84, and a switching transistor 86 to provide a switching output at the output terminals 87 and 88. The remainder of the system shown in FIG. 4 is substantially the same as the system shown in FIG. 3, it being noted that the potentiometer 36 in FIG. 4 is to be connected to connection point A as designated in FIG. 3.

The output means 62 receives the demodulated signal from conductor 49 and the capacitor 63 and coils 64 and 66 of the first filtering circuit filters out the frequency components of the signal which are below the frequency of the patient body condition being monitored, for example, the pulse rate of a patient. The filtered signal is amplified by the transistor 67 of the amplification circuit to compensate for the signal loss in the first filtering circuit and the amplified filtered signal is then passed through the capacitors 74 and 76, and choke coil 77 of the second filtering circuit. The second filtering circuit removes the frequency components of those signals above the patient's pulse rate so as to produce a signal which is primarily a function of the pulse rate of the patient being monitored. This signal may be recorded or visually observed by connecting appropriate equipment to the jack 79.

As long as the pulse rate is present a signal will be produced to provide an input level across the resistors 82 and 83 sufficient to keep the driver transistor 84 turned on, whereby with the circuit configuration shown the switching transistor 86 will continue in operation. The operation of the transistor 86 provides the indication that the patient's pulse rate is present. If the pulse stops, the signal at the base of the driver transistor 84 will terminate thereby turning off the switching transistor 86 to actuate any suitable alarm.

Although the invention has been described with respect to preferred embodiments thereof it is to be understood that it is not to be so limited since changes and modifications can be made therein which are within the full intended scope of the invention as defined by the appended claims.

I claim:
1. A patient monitoring system comprising:
   a. an electrically insulated capacitive element device having one side positionable adjacent a patient to be monitored, said capacitive element device including a main conductive element,
   b. a carrier means connectable in an electrical circuit with the capacitive element device for producing a carrier frequency signal to set up an electric field around the main conductive element, said carrier frequency signal modulated by patient movement,
   c. an amplifying means connected to be responsive to the capacitive element device and connected to receive the modulated carrier signal,
   d. an electrical shield means connected to the amplifying means to confine the electric field around the main conductive element to said one side of the capacitive element device,
   e. a demodulating means connected to receive the modulated carrier signal and demodulate said modulated carrier signal to produce a demodulated signal varying as a function of the preselected electrical characteristic of the capacitive element device; and
   f. an output means responsive to the demodulated signal for producing an output signal.
2. A patient monitoring system according to claim 1 wherein:
   a. said main conductive element comprises a main conductive foil sheet,
   b. said capacitive element device comprises a multilayer sheet assembly having the main conductive foil sheet enclosed between upper and lower nonconducting sheets, and
   c. means connecting the amplifying means to be responsive to said main conductive foil sheet.
3. A patient monitoring system according to claim 2 wherein:
   a. said electrical shield means comprises a shield foil sheet of conductive material interposed between the upper and lower nonconducting sheets of the capacitive element device,
   b. said capacitive element device additionally includes an electrically insulating sheet for separating the main conductive foil sheet from the shield foil sheet, and
   c. said shield foil sheet connected to the amplifying means to provide an electrical shield for said main conductive foil sheet.
4. A patient monitoring system according to claim 2, wherein:
   a. said demodulating means comprises a detector, connected to receive the modulated carrier signal, a filtering circuit electrically connected to and between the amplifying means and the detector, and an amplifier connected to receive the input therefor from the detector to produce an amplified demodulated signal.
5. A patient monitoring system according to claim 2 including:
   a. a voltage divider circuit for producing an input for said amplifying means said voltage divider circuit including the capacitive element device, and
   b. said capacitive element device and said amplifying means connected to one another such that said amplifying means receives the input from said voltage divider circuit and wherein said carrier means is connected to said voltage divider circuit to apply the carrier frequency signal across said voltage divider circuit.
6. A patient monitoring system according to claim 2 wherein:
   a. said output means includes means for producing an output signal varying as a function of the demodulated signal.
7. A patient monitoring system according to claim 6 wherein:
   a. said electrical shield means comprises a shield foil sheet of conductive material interposed between the upper and lower nonconducting sheets of the capacitive element device,
   b. said capacitive element device additionally includes an electrically insulating sheet for separating the main conductive foil sheet from the shield foil sheet, and
   c. said shield foil sheet is connected to the amplifying means to provide an electrical shield for said main conductive foil sheet.
8. A patient monitoring device according to claim 6 wherein:
   a. said output means additionally includes means for interpreting the output signal of the demodulating means to produce an alarm signal when selected characteristics occur in said output signal of the demodulating means.
9. A patient monitoring system according to claim 8 including:
   a. an electrical power supply,
   b. means for connecting the monitoring system to said power supply, and
   c. said demodulating means comprising a circuit for filtering out any incidental leakage into the system from said power supply.
10. A patient monitoring system according to claim 1 wherein:
    a. said output means includes a means for producing an output signal varying as a function of the demodulated signal.
11. A patient monitoring device according to claim 1 wherein:
    a. said output means includes means for interpreting the output signal of the demodulating means to produce an alarm signal when selected characteris- tics occur in said output signal of the demodulating means.

12. A patient monitoring system according to claim 1 including:
 a. an electrical power supply, and
 b. means for connecting the monitoring system to said power supply,
 c. said demodulating means comprising a circuit for filtering out any incidental leakage into the system from said power supply.

13. A patient monitoring system according to claim 1 including:
 a. a voltage divider circuit for producing an input for said amplifying means, said voltage divider circuit including the capacitive element device, and
 b. said capacitive element device and said amplifying means connected to one another such that said amplifying means receives the input from said voltage divider circuit and wherein said carrier means is connected to said voltage divider circuit to apply the carrier frequency signal across said divider circuit.

14. A patient monitoring system according to claim 13 wherein:
 a. said output means includes means for producing an output signal varying as a function of the demodulated signal.

15. A patient monitoring system according to claim 1 wherein:
 a. said main conductive element comprises a main conductive foil sheet,
 b. said electrical shield means comprises a shield foil sheet, and
 c. said capacitive element device includes
  1. a cover means composed of an electrically non-conducting waterproof material enclosing the main conductive foil sheet and the shield foil sheet, a pair of electrically conductive foil sheets within said cover means,
  2. an electrically insulating sheet arranged between said main conductive foil sheet and the shield foil sheet, and
  3. a shielded cable having a center conductor connected to the main conductive foil sheet and a shield conductor connected to the shield foil sheets,
 d. said amplifying means connected to be responsive to said center conductor to electrically shield said main conductive foil sheet from said shield foil sheet.

16. A patient monitoring system according to claim 15 wherein:
 a. said amplifying means includes an input circuit connected to receive the carrier signal and connected to said center conductor of the shielded cable so as to produce a carrier signal frequency output modulated by the signal received from said center conductor.

17. A patient monitoring system according to claim 16 wherein:
 a. said demodulating means includes a filtering and detecting circuit connected to receive the modulated output of said amplifying means to produce an output varying in proportion to the signal received from said center conductor.

18. A patient monitoring system according to claim 1 wherein:
 a. said output means includes a patient pulse rate monitoring circuit having filter circuits connected to receive the output of the demodulating means and to filter out substantially all signals below and above a selected frequency level corresponding to a predetermined pulse rate; including, additionally, an alarm signal circuit responsive to the absence of a signal from said filter circuits for a preselected time to produce an alarm signal.

19. A patient monitoring system according to claim 1 wherein:
 a. said preselected electrical characteristic is the impedance provided to the amplifying means.

20. A patient monitoring system according to claim 19 wherein:
 a. said impedance varies as a function of the capacitive coupling between the capacitive element device and the patient being monitored.

21. A method of monitoring selected body conditions of a patient comprising:
 a. placing an electrically insulated capacitive element adjacent the body of the patient;
 b. applying a suitable carrier frequency signal to the capacitive element with an appropriate electrical circuit to modulate said carrier signal with an electrical characteristic of said capacitive element that varies with the patient body condition;
 c. placing a shielding element of electrically conductive material adjacent to and electrically insulated from said capacitive element in a position such that the capacitive element is between the patient and said shielding element;
 d. connecting said shielding element into said electrical circuit to provide a shielding effect from undesired interference sources,
 e. demodulating the modulated carrier signal; and
 f. interpreting the demodulated carrier signal to determine a selected body condition of the patient.

* * * * *